(12) United States Patent
Leven

(10) Patent No.: US 9,415,154 B2
(45) Date of Patent: Aug. 16, 2016

(54) SYSTEMS AND METHODS FOR MAKING AND USING AN ELECTRICAL STIMULATION SYSTEM WITH PHOTONIC STIMULATION CAPABILITIES

(71) Applicant: BOSTON SCIENTIFIC NEUROMODULATION CORPORATION, Valencia, CA (US)

(72) Inventor: Jacob B. Leven, Huntington Beach, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 391 days.

(21) Appl. No.: 14/076,860

(22) Filed: Nov. 11, 2013

(65) Prior Publication Data

US 2014/0148753 A1    May 29, 2014

Related U.S. Application Data

(60) Provisional application No. 61/729,732, filed on Nov. 26, 2012.

(51) Int. Cl.
| | |
|---|---|
| *A61N 1/30* | (2006.01) |
| *A61M 5/00* | (2006.01) |
| *A61N 1/05* | (2006.01) |
| *A61N 5/06* | (2006.01) |
| *A61N 1/36* | (2006.01) |
| *A61M 5/142* | (2006.01) |

(52) U.S. Cl.
CPC .. *A61M 5/00* (2013.01); *A61N 1/05* (2013.01); *A61N 1/0551* (2013.01); *A61N 5/0601* (2013.01); *A61N 5/0622* (2013.01); *A61M 5/14276* (2013.01); *A61M 2210/1003* (2013.01); *A61N 1/0553* (2013.01); *A61N 1/3605* (2013.01); *A61N 2005/065* (2013.01)

(58) Field of Classification Search
CPC ..... A61N 1/0551; A61N 1/0534; A61N 1/05; A61N 1/0553; A61N 5/0622; A61M 5/14276
See application file for complete search history.

(56) References Cited

U.S. PATENT DOCUMENTS

| | | | | | |
|---|---|---|---|---|---|
| 5,169,395 | A | * | 12/1992 | Narciso, Jr. ............ | A61N 5/062 606/14 |
| 5,298,018 | A | * | 3/1994 | Narciso, Jr. .......... | A61K 31/555 128/898 |
| 5,474,528 | A | * | 12/1995 | Meserol ................. | A61N 5/062 604/20 |
| 5,728,068 | A | * | 3/1998 | Leone ..................... | A61F 2/958 604/101.01 |
| 6,181,969 | B1 | | 1/2001 | Gord | |
| 6,231,593 | B1 | * | 5/2001 | Meserol ................. | A61F 13/02 604/20 |

(Continued)

*Primary Examiner* — Aarti B Berdichevsky
(74) *Attorney, Agent, or Firm* — Lowe Graham Jones PLLC; Bruce E. Black

(57) ABSTRACT

An electrical stimulation lead includes electrodes disposed along a distal end portion of a lead body; terminals disposed along a proximal end portion of the lead body; and stimulation conductors electrically coupling the terminals to the electrodes. A light-emitter is disposed along the distal end portion of the lead body. A light source is disposed along the at least one lead body and converts received electrical power into light. An optical transport medium is disposed along the at least one lead body. The optical transport medium extends between the light source and the light-emitter. A light source conductor electrically couples the light source and the terminals. A drug-dispensing port is defined along the distal end portion of the lead body. A drug-delivery channel is in fluid communication with the at least one drug-dispensing port and extends to the proximal end portion of the lead body.

20 Claims, 10 Drawing Sheets

(56) References Cited

U.S. PATENT DOCUMENTS

| | | |
|---|---|---|
| 6,516,227 B1 | 2/2003 | Meadows et al. |
| 6,609,029 B1 | 8/2003 | Mann et al. |
| 6,609,032 B1 | 8/2003 | Woods et al. |
| 6,741,892 B1 | 5/2004 | Meadows et al. |
| 6,832,115 B2 | 12/2004 | Borkan |
| 7,244,150 B1 | 7/2007 | Brase et al. |
| 7,437,193 B2 | 10/2008 | Parramon et al. |
| 7,672,734 B2 | 3/2010 | Anderson et al. |
| 7,761,165 B1 | 7/2010 | He et al. |
| 7,949,395 B2 | 5/2011 | Kuzma |
| 7,974,706 B2 | 7/2011 | Moffitt et al. |
| 8,175,710 B2 | 5/2012 | He |
| 8,224,450 B2 | 7/2012 | Brase |
| 8,364,278 B2 | 1/2013 | Pianca et al. |
| 8,685,005 B2 * | 4/2014 | Dahm ................ A61N 5/0601 128/898 |
| 8,892,216 B2 * | 11/2014 | Leven .................. A61N 1/05 604/175 |
| 9,180,291 B2 * | 11/2015 | Leven .................. A61N 1/0553 |
| 2006/0155348 A1 | 7/2006 | deCharms |
| 2007/0150036 A1 | 6/2007 | Anderson |
| 2010/0070002 A1 * | 3/2010 | Hyde .................. A61B 5/06 607/60 |
| 2010/0106204 A1 * | 4/2010 | Moffitt ................ A61N 1/37 607/2 |
| 2010/0268298 A1 | 10/2010 | Moffitt et al. |
| 2011/0005069 A1 | 1/2011 | Pianca |
| 2011/0016378 A1 | 1/2011 | Rothschild |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0238129 A1 | 9/2011 | Moffitt et al. |
| 2011/0313500 A1 | 12/2011 | Barker et al. |
| 2012/0016378 A1 | 1/2012 | Pianca et al. |
| 2012/0046710 A1 | 2/2012 | DiGiore et al. |
| 2012/0071949 A1 | 3/2012 | Pianca et al. |
| 2013/0274844 A1 * | 10/2013 | Leven .................. A61N 1/0551 607/116 |
| 2013/0282091 A1 * | 10/2013 | Leven .................. A61N 1/0553 607/116 |
| 2013/0317588 A1 * | 11/2013 | Howard ............... A61N 1/0551 607/118 |
| 2014/0018884 A1 * | 1/2014 | Leven .................... A61N 1/05 607/72 |
| 2014/0039586 A1 * | 2/2014 | Barker ................ A61N 1/0551 607/116 |
| 2014/0058488 A1 * | 2/2014 | Leven .................... A61N 1/05 607/116 |
| 2014/0155968 A1 * | 6/2014 | Govea ................ A61N 1/0553 607/116 |
| 2014/0155969 A1 * | 6/2014 | Leven .................. A61N 1/0551 607/116 |
| 2014/0180371 A1 * | 6/2014 | Leven .................. A61N 1/0551 607/116 |
| 2014/0323924 A1 | 10/2014 | Mishelevich |
| 2015/0018634 A1 * | 1/2015 | Zhu .................... A61B 5/0205 600/301 |

\* cited by examiner

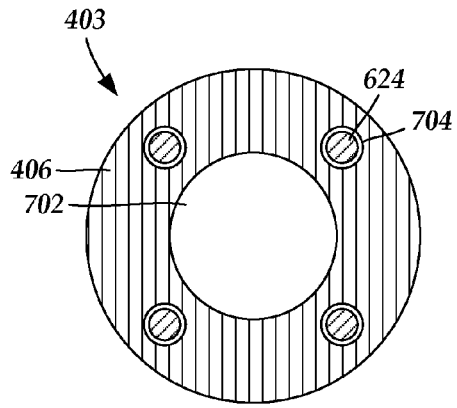
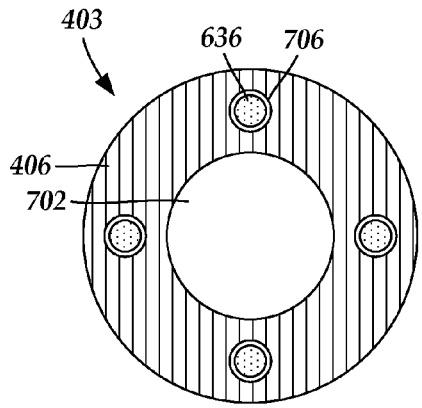
Fig. 7A  Fig. 7B
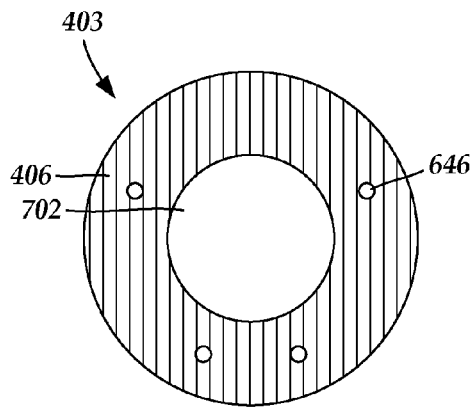
Fig. 7C
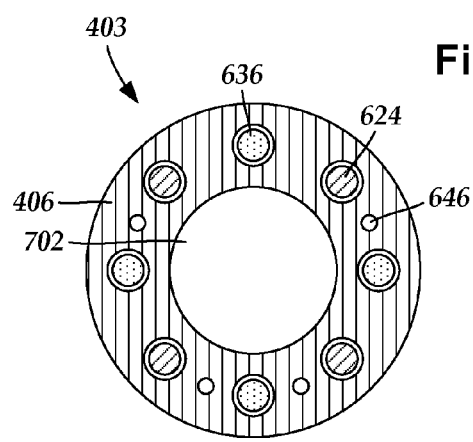
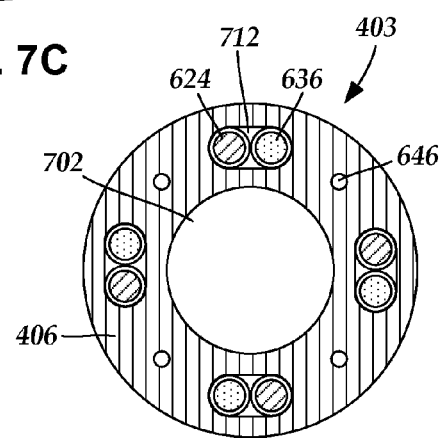
Fig. 7D  Fig. 7E

SYSTEMS AND METHODS FOR MAKING AND USING AN ELECTRICAL STIMULATION SYSTEM WITH PHOTONIC STIMULATION CAPABILITIES

CROSS-REFERENCE TO RELATED APPLICATIONS

This application claims the benefit under 35 U.S.C. §119 (e) of U.S. Provisional Patent Application Ser. No. 61/729,732 filed on Nov. 26, 2012, which is incorporated herein by reference.

FIELD

The present invention is directed to the area of implantable electrical stimulation systems and methods of making and using the systems. The present invention is also directed to implantable electrical stimulation leads having electrodes, light-emitters, and drug-dispensing ports, as well as methods of making and using the leads, electrodes, light-emitters, drug-dispensing ports, and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

Delivering drugs at a specific site, such as in proximity to neural tissue in the spine or brain, can be used for treating a number of different indications, as well as for providing gene therapy. Additionally, site-specific delivery of drugs may reduce the amount of the drug needed for obtaining efficacious treatment, as well as reducing potentially adverse side-effects caused from uptake of the drugs at other, undesirable locations within the patient. Photonic stimulation may also be used for treating a number of different indications. Additionally, photonic stimulation may be used in combination with site-specific drug delivery. For example, optogenetics is a field where light is used to control neural activity in combination with drug delivery.

BRIEF SUMMARY

In one embodiment, an electrical stimulation lead includes at least one lead body having a distal end portion, a proximal end portion, an outer surface, and a longitudinal length. A plurality of electrodes is disposed along the distal end portion of the at least one lead body. A plurality of terminals is disposed along the proximal end portion of the at least one lead body. A plurality of stimulation conductors electrically couples each of the plurality of terminals to at least one of the plurality of electrodes. At least one light-emitter is disposed along the distal end portion of the at least one lead body. The at least one light-emitter is configured and arranged for emitting received light outward from the outer surface of the lead body. At least one light source is disposed along the at least one lead body. The at least one light source is configured and arranged for converting received electrical power into light. At least one optical transport medium is disposed along the at least one lead body. The at least one optical transport medium has a proximal end coupled to the at least one light source and a distal end coupled to the at least one light-emitter. The at least one optical transport medium is configured and arranged to transport light from the at least one light source to the at least one light-emitter. At least one light source conductor is electrically coupled to the at least one light source and extends to the plurality of terminals. At least one drug-dispensing port is defined along the distal end portion of the at least one lead body. At least one drug-delivery channel is in fluid communication with the at least one drug-dispensing port. The at least one drug-delivery channel extends along the longitudinal length of the lead body to the proximal end portion of the lead body.

In another embodiment, an electrical stimulation lead includes at least one lead body having a distal end portion, a proximal end portion, an outer surface, and a longitudinal length. A plurality of electrodes is disposed along the distal end portion of the at least one lead body. A plurality of terminals is disposed along the proximal end portion of the at least one lead body. A plurality of stimulation conductors electrically couples each of the plurality of terminals to at least one of the plurality of electrodes. At least one light-emitter is disposed along the distal end portion of the at least one lead body. The at least one light-emitter is configured and arranged for receiving power, converting the received power to light, and emitting the converted light outward from the outer surface of the lead body. At least one light source conductor is coupled to the at least one light-emitter and extends to the plurality of terminals. At least one drug-dispensing port is defined along the distal end portion of the at least one lead body. At least one drug-delivery channel is in fluid communication with the at least one drug-dispensing port. The at least one drug-delivery channel extends along the longitudinal length of the lead body to the proximal end portion of the lead body.

In yet another embodiment, an electrical stimulation lead assembly includes an electrical stimulation lead and at least one light source. The electrical stimulation lead includes at least one lead body having a distal end portion, a proximal end portion, an outer surface, and a longitudinal length. A plurality of electrodes is disposed along the distal end portion of the at least one lead body. A plurality of terminals is disposed along the proximal end portion of the at least one lead body. A plurality of stimulation conductors electrically couples each of the plurality of terminals to at least one of the plurality of electrodes. At least one light-emitter is disposed along the distal end portion of the at least one lead body. The at least one light-emitter is configured and arranged for emitting received light outward from the outer surface of the lead body. At least one optical transport medium is disposed along the at least one lead body. The at least one optical transport medium has a distal end coupled to the at least one light-emitter and a proximal end extending to the proximal end portion of the lead body. The at least one optical transport medium is configured and arranged to transport light. At least one drug-dispensing port is defined along the distal end portion of the at least one lead body. At least one drug-delivery channel is in fluid communication with the at least one drug-dispensing port. The at least one drug-delivery channel extends along the longitudinal length of the lead body to the proximal end portion of the lead body. The at least one light source is disposed external to the at least one lead body and is in communication with the at least one optical transport medium. The at least one light source is configured and arranged for generating light. The at least one light source is coupled to the at least one light-emitter via the at least one optical transport medium.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 7A is a schematic transverse cross-sectional view of one embodiment of the lead body of FIG. 6A, where the lead body defines a stylet lumen and optical lumens, and where optical transport media are disposed in the optical lumens, according to the invention;

FIG. 7B is a schematic transverse cross-sectional view of one embodiment of the lead body of FIG. 6B, where the lead body defines a stylet lumen and stimulation lumens, and where stimulation conductors are disposed in the stimulation lumens, according to the invention;

FIG. 7C is a schematic transverse cross-sectional view of one embodiment of the lead body of FIG. 6C, where the lead body defines a stylet lumen and drug-delivery channels, according to the invention;

FIG. 7D is a schematic transverse cross-sectional view of one embodiment of the lead body of FIG. 4A, where the lead body defines a stylet lumen, optical lumens, stimulation lumens, and drug-delivery channels, where optical transport media are disposed in the optical lumens, and where stimulation conductors are disposed in the stimulation lumens, according to the invention;

FIG. 7E is a schematic transverse cross-sectional view of one embodiment of the lead body of FIG. 4A, where the lead body defines a stylet lumen, drug-delivery channels, and combination lumens, and where optical transport media and stimulation conductors are each disposed in the combination lumens, according to the invention;

DETAILED DESCRIPTION

The present invention is directed to the area of implantable electrical stimulation systems and methods of making and using the systems. The present invention is also directed to implantable electrical stimulation leads having electrodes, light-emitters, and drug-dispensing ports, as well as methods of making and using the leads, electrodes, light-emitters, drug-dispensing ports, and electrical stimulation systems.

Suitable implantable electrical stimulation systems include, but are not limited to, a least one lead with one or more electrodes disposed along a distal end of the lead and one or more terminals disposed along the one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,949,395; 7,244,150; 7,672,734; 7,761,165; 7,974,706; 8,175,710; 8,224,450; and 8,364,278; and U.S. Patent Application Publication No. 2007/0150036, all of which are incorporated by reference.

Figure 1:
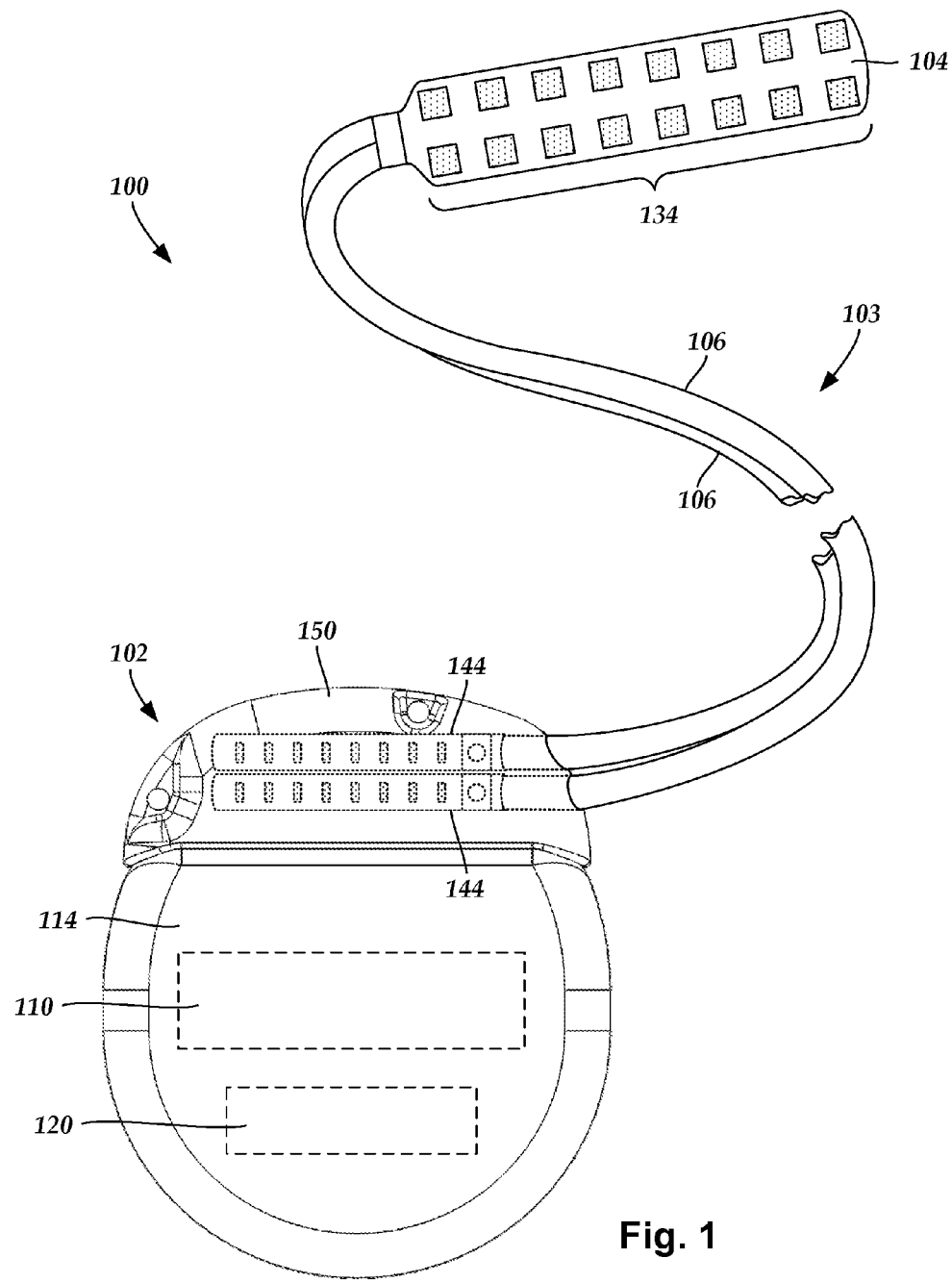
FIG. 1 is a schematic view of one embodiment of an electrical stimulation system that includes a paddle lead electrically coupled to a control module, according to the invention.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 includes a paddle body 104 and one or more lead bodies 106. In FIG. 1, the lead 103 is shown having two lead bodies 106. It will be understood that the lead 103 can include any suitable number of lead bodies including, for example, one, two, three, four, five, six, seven, eight or more lead bodies 106. An array of electrodes 133, such as electrode 134, is disposed on the paddle body 104, and an array of terminals (e.g., 310 in FIGS. 3A-3B) is disposed along each of the one or more lead bodies 106.

It will be understood that the electrical stimulation system can include more, fewer, or different components and can have a variety of different configurations including those configurations disclosed in the electrical stimulation system references cited herein. For example, instead of a paddle body, the electrodes can be disposed in an array at or near the distal end of a lead body forming a percutaneous lead.

Figure 2:
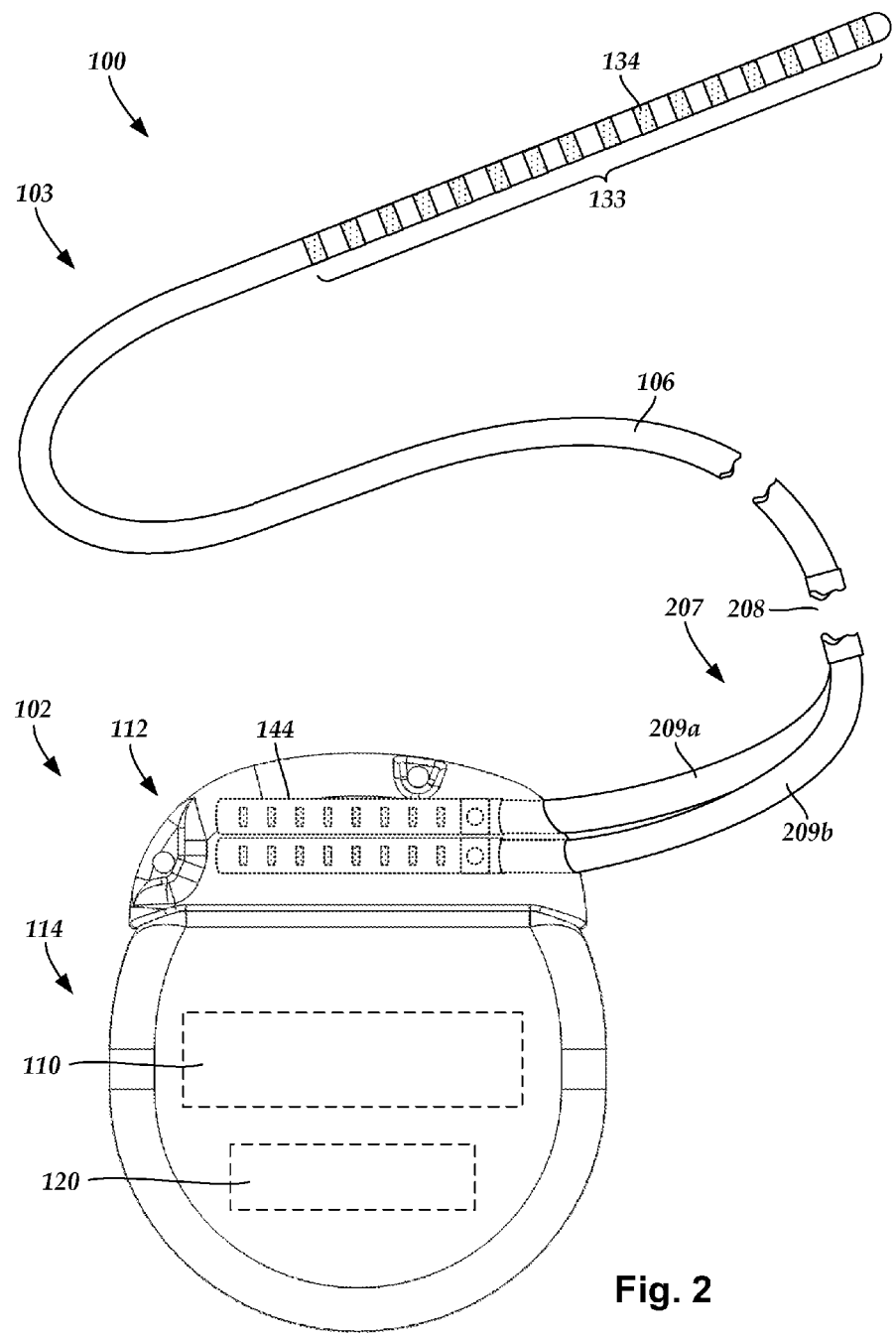
FIG. 2 is a schematic view of one embodiment of an electrical stimulation system that includes a percutaneous lead electrically coupled to a control module, according to the invention.

FIG. 2 illustrates schematically another embodiment of the electrical stimulation system 100, where the lead 103 is a percutaneous lead. In FIG. 2, the electrodes 134 are shown disposed along the one or more lead bodies 106. In at least some embodiments, the lead 103 is isodiametric along a longitudinal length of the lead body 106.

The lead 103 can be coupled to the control module 102 in any suitable manner. In FIG. 1, the lead 103 is shown coupling directly to the control module 102. In at least some other embodiments, the lead 103 couples to the control module 102 via one or more intermediate devices (300 in FIGS. 3A-3B). For example, in at least some embodiments one or more lead extensions 324 (see e.g., FIG. 3B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

In FIG. 2, the electrical stimulation system 100 is shown having a splitter 207 configured and arranged for facilitating coupling of the lead 103 to the control module 102. The splitter 207 includes a splitter connector 208 configured to couple to a proximal end of the lead 103, and one or more splitter tails 209a and 209b configured and arranged to couple to the control module 102 (or another splitter, a lead extension, an adaptor, or the like).

The control module 102 typically includes a connector housing 112 and a sealed electronics housing 114. An electronic subassembly 110 and an optional power source 120 are disposed in the electronics housing 114. A control module connector 144 is disposed in the connector housing 112. The control module connector 144 is configured and arranged to make an electrical connection between the lead 103 and the electronic subassembly 110 of the control module 102.

The electrical stimulation system or components of the electrical stimulation system, including the paddle body 104, the one or more of the lead bodies 106, and the control module 102, are typically implanted into the body of a patient. The electrical stimulation system can be used for a variety of applications including, but not limited to deep brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium.

Any suitable number of electrodes 134 can be disposed on the lead including, for example, four, five, six, seven, eight, nine, ten, eleven, twelve, fourteen, sixteen, twenty-four, thirty-two, or more electrodes 134. In the case of paddle leads, the electrodes 134 can be disposed on the paddle body 104 in any suitable arrangement. In FIG. 1, the electrodes 134 are arranged into two columns, where each column has eight electrodes 134.

The electrodes of the paddle body 104 (or one or more lead bodies 106) are typically disposed in, or separated by, a non-conductive, biocompatible material such as, for example, silicone, polyurethane, polyetheretherketone ("PEEK"), epoxy, and the like or combinations thereof. The one or more lead bodies 106 and, if applicable, the paddle body 104 may be formed in the desired shape by any process including, for example, molding (including injection molding), casting, and the like. The non-conductive material typically extends from the distal ends of the one or more lead bodies 106 to the proximal end of each of the one or more lead bodies 106.

In the case of paddle leads, the non-conductive material typically extends from the paddle body 104 to the proximal end of each of the one or more lead bodies 106. Additionally, the non-conductive, biocompatible material of the paddle body 104 and the one or more lead bodies 106 may be the same or different. Moreover, the paddle body 104 and the one or more lead bodies 106 may be a unitary structure or can be formed as two separate structures that are permanently or detachably coupled together.

Figure 3A:
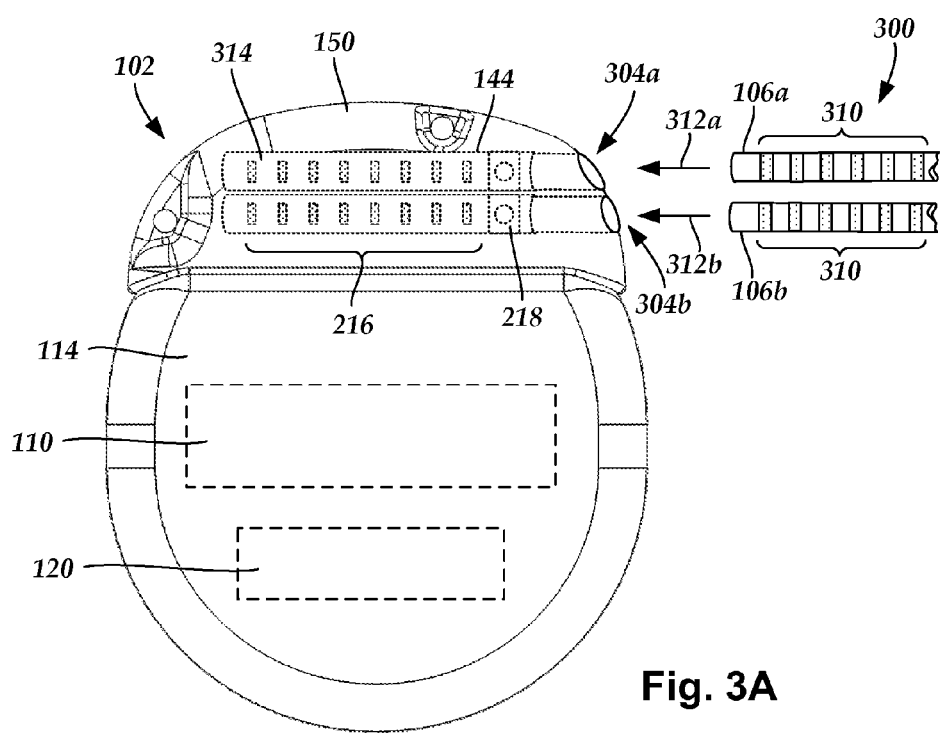
FIG. 3A is a schematic view of one embodiment of the control module of FIG. 1 configured and arranged to electrically couple to an elongated device, according to the invention.
Figure 3B:
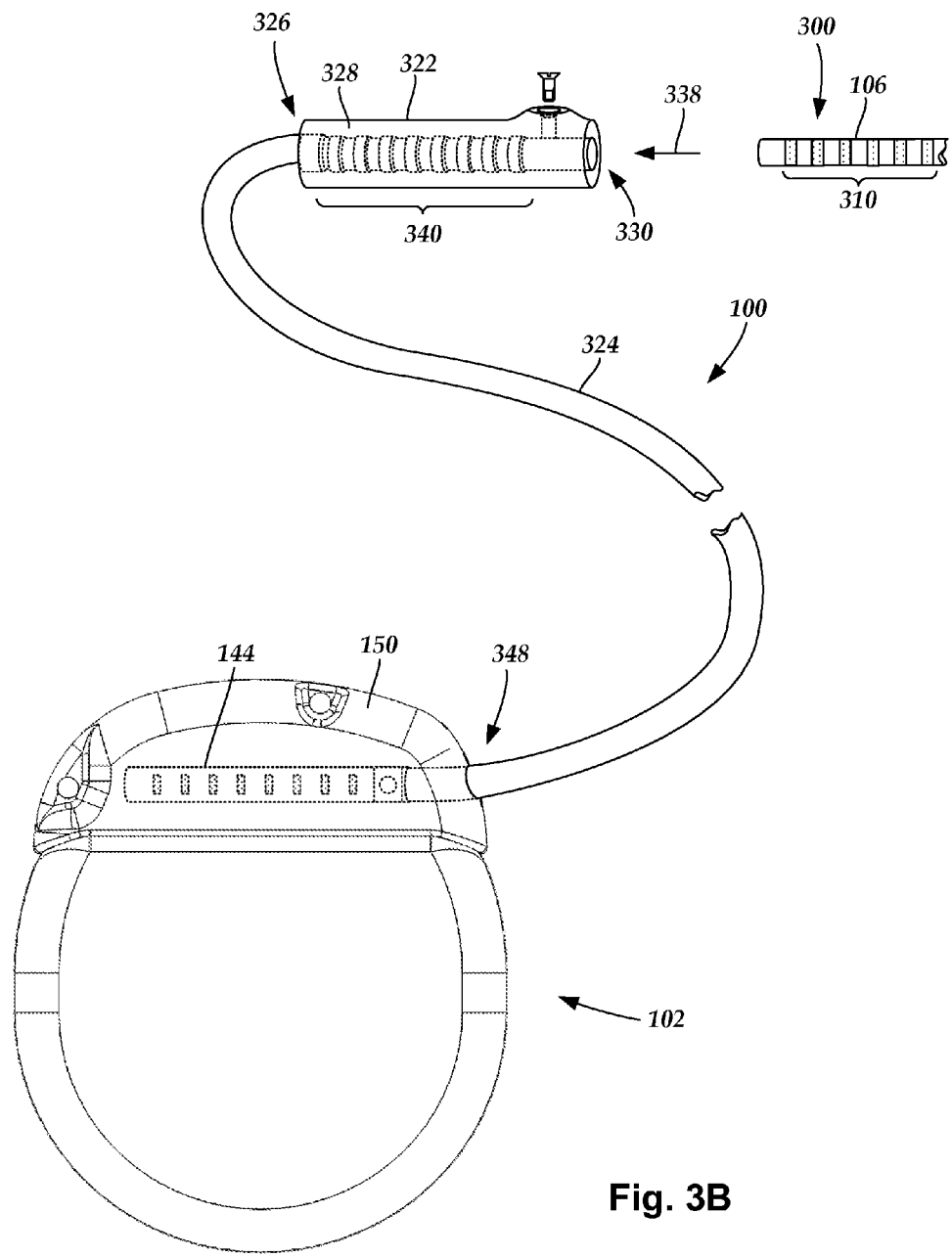
FIG. 3B is a schematic view of one embodiment of a lead extension configured and arranged to electrically couple the elongated device of FIG. 2A to the control module of FIG. 1, according to the invention.

Terminals (e.g., 310 in FIGS. 3A-3B) are typically disposed along the proximal end of the one or more lead bodies 106 of the electrical stimulation system 100 (as well as any splitters, lead extensions, adaptors, or the like) for electrical connection to corresponding connector contacts (e.g., 314 in FIGS. 3A-3B). The connector contacts are disposed in connectors (e.g., 144 in FIGS. 1-3B; and 322 FIG. 3B) which, in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors extend through a lumen. There may also be one or more lumens (not shown) that open at, or near, the proximal end of the one or more lead bodies 106, for example, for inserting a stylet to facilitate placement of the one or more lead bodies 106 within a body of a patient. Additionally, there may also be one or more lumens (not shown) that open at, or near, the distal end of the one or more lead bodies 106, for example, for infusion of drugs or medication into the site of implantation of the one or more lead bodies 106. In at least one embodiment, the one or more lumens are flushed continually, or on a regular basis, with saline, epidural fluid, or the like. In at least some embodiments, the one or more lumens are permanently or removably sealable at the distal end.

FIG. 3A is a schematic side view of one embodiment of a proximal end of one or more elongated devices 300 configured and arranged for coupling to one embodiment of the control module connector 144. The one or more elongated devices may include, for example, one or more of the lead bodies 106 of FIG. 1, one or more intermediate devices (e.g., a splitter, the lead extension 324 of FIG. 3B, an adaptor, or the like or combinations thereof), or a combination thereof.

The control module connector 144 defines at least one port into which a proximal end of the elongated device 300 can be inserted, as shown by directional arrows 312a and 312b. In FIG. 3A (and in other figures), the connector housing 112 is shown having two ports 304a and 304b. The connector housing 112 can define any suitable number of ports including, for example, one, two, three, four, five, six, seven, eight, or more ports.

The control module connector 144 also includes a plurality of connector contacts, such as connector contact 314, disposed within each port 304a and 304b. When the elongated device 300 is inserted into the ports 304a and 304b, the connector contacts 314 can be aligned with a plurality of terminals 310 disposed along the proximal end(s) of the elongated device(s) 300 to electrically couple the control module 102 to the electrodes (134 of FIG. 1) disposed on the paddle body 104 of the lead 103. Examples of connectors in control modules are found in, for example, U.S. Pat. Nos. 7,244,150 and 8,224,450, which are incorporated by reference.

FIG. 3B is a schematic side view of another embodiment of the electrical stimulation system 100. The electrical stimulation system 100 includes a lead extension 324 that is configured and arranged to couple one or more elongated devices 300 (e.g., one of the lead bodies 106 of FIGS. 1 and 2, the splitter 207 of FIG. 2, an adaptor, another lead extension, or the like or combinations thereof) to the control module 102. In FIG. 3B, the lead extension 324 is shown coupled to a single port 304 defined in the control module connector 144. Additionally, the lead extension 324 is shown configured and arranged to couple to a single elongated device 300. In alternate embodiments, the lead extension 324 is configured and arranged to couple to multiple ports 304 defined in the control module connector 144, or to receive multiple elongated devices 300, or both.

A lead extension connector 322 is disposed on the lead extension 324. In FIG. 3B, the lead extension connector 322 is shown disposed at a distal end 326 of the lead extension 324. The lead extension connector 322 includes a connector housing 328. The connector housing 328 defines at least one port 330 into which terminals 310 of the elongated device 300 can be inserted, as shown by directional arrow 338. The connector housing 328 also includes a plurality of connector contacts, such as connector contact 340. When the elongated device 300 is inserted into the port 330, the connector contacts 240 disposed in the connector housing 328 can be aligned with the terminals 310 of the elongated device 300 to electrically couple the lead extension 324 to the electrodes (134 of FIGS. 1 and 2) disposed along the lead (103 in FIGS. 1 and 2).

In at least some embodiments, the proximal end of the lead extension 324 is similarly configured and arranged as a proximal end of the lead 103 (or other elongated device 300). The lead extension 324 may include a plurality of electrically conductive wires (not shown) that electrically couple the connector contacts 340 to a proximal end 348 of the lead extension 324 that is opposite to the distal end 326. In at least some embodiments, the conductive wires disposed in the lead extension 324 can be electrically coupled to a plurality of terminals (not shown) disposed along the proximal end 348 of the lead extension 324. In at least some embodiments, the proximal end 348 of the lead extension 324 is configured and arranged for insertion into a connector disposed in another lead extension (or another intermediate device). In other embodiments (and as shown in FIG. 3B), the proximal end 348 of the lead extension 324 is configured and arranged for insertion into the control module connector 144.

Figures 4A, 4B, 4C:
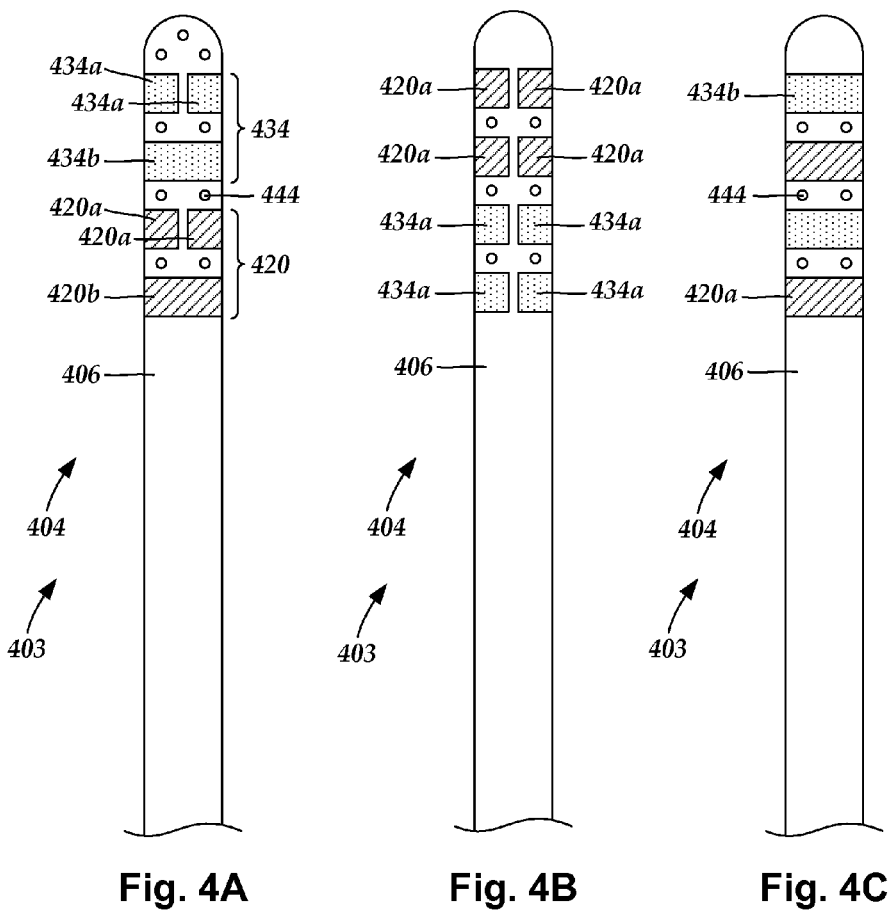
FIG. 4A is a schematic side view of one embodiment of electrodes, light-emitters, and drug-dispensing ports disposed along a distal end portion of a lead body, according to the invention.
FIG. 4B is a schematic side view of a second embodiment of electrodes, light-emitters, and drug-dispensing ports disposed along a distal end portion of the lead body of FIG. 4A, according to the invention.
FIG. 4C is a schematic side view of a third embodiment of electrodes, light-emitters, and drug-dispensing ports disposed along a distal end portion of the lead body of FIG. 4A, according to the invention.

Turning to FIG. 4A, in some instances it may be beneficial to design electrical stimulation leads (e.g., percutaneous leads, paddle leads, or the like) to enable photonic stimulation, or site-specific drug delivery, or both. In some cases, electrical stimulation from the electrodes may be used in combination with photonic stimulation, site-specific drug delivery, or both. Alternately or additionally, the electrodes of the electrical stimulation system can be used for facilitating placement of the lead within the patient.

It may be advantageous to combine site-specific drug delivery with photonic stimulation to provide various types of gene therapy. In some instances, delivery of drugs to specific neural cells may make those cells more sensitive to photonic stimulation. Electrical stimulation may further enhance therapy regimes that utilize photonic stimulation, or site-specific drug delivery, or both. Additionally, electrodes of electrical stimulation systems may be used to detect electrical activity, thereby providing a mechanism for facilitating detection of potential target therapy locations, as well as placement of the lead in operational proximity to potential target therapy locations.

In at least some embodiments, photonic stimulation, site-specific drug delivery, and electrical stimulation are each configured and arranged to operate independently of each other. In at least some embodiments, photonic stimulation, site-specific drug delivery, and electrical stimulation are configured and arranged to operate together, either concurrently, or sequentially, or any combination thereof.

FIG. 4A is a schematic side view of one embodiment of a portion of a lead 403. In FIG. 4A, multiple light-emitters 420, multiple electrodes 434, and multiple drug-dispensing ports 444 are shown disposed along a distal end portion 404 of a lead body 406 of the lead 403.

The light-emitters 420 can be formed in any shape or size suitable for an implantable device, such as the lead 403, and for providing photonic stimulation to neural tissue. In FIG. 4A, some of the light-emitters 420 are shown as being ring-shaped, such as ring-shaped light-emitter 420b, where the light-emitter 420b extends around an entire circumference of the lead body 406.

Additionally, in FIG. 4A some of the light-emitters 420 are shown as being segmented, such as segmented light-emitters 420a, where the segmented light-emitter 420a extends around less than an entire circumference of the lead body 406. In at least some embodiments, segmented light-emitters 420a are arranged into groups of two or more segmented light-emitters 420a that each extend partway around a given circumference of the lead body 406. In FIG. 4A (and in other figures) the segmented light-emitters 420a are shown in groups of two, where each of the two segmented light-emitters 420a extends partway around a given circumference of the lead body 406.

It will be understood that the light-emitters 420 may be formed in any suitable shape including, for example, round, oval, rectangular, pentagonal, cruciform, star-shaped, or the like. Any suitable number of light-emitters 420 may be disposed along the distal end portion 404 of the lead body 406 including, for example, one, two, three, four, five, six, seven, eight, nine, ten, eleven, twelve, fourteen, sixteen, twenty, twenty-four, thirty, thirty-six, forty, forty-eight, fifty, or more light-emitters 420. It may be advantageous to include light-emitters 420 with shapes, sizes, and numbers that are suited for providing photonic stimulation to desired tissue, while also avoiding undesired stimulation of non-targeted tissue.

Similarly, the electrodes 434 can be formed in any shape or size suitable for disposing on an implantable device, such as the lead 403. In FIG. 4A, some of the electrodes 434 are shown as being ring-shaped, such as ring-shaped electrode 434b, where the electrode 434b extends around an entire circumference of the lead body 406.

Additionally, in FIG. 4A some of the electrodes 434 are shown as being segmented, such as segmented electrode 434a, where the electrode 420a extends around less than an entire circumference of the lead body 406. In at least some embodiments, segmented electrodes 434a are arranged into groups of two or more segmented electrodes 434a that each extend partway around a given circumference of the lead body 406. In FIG. 4A (and in other figures) the segmented electrodes 434a are shown in groups of two, where each of the two segmented electrodes 434a extends partway around a given circumference of the lead body 406.

Examples of segmented electrodes disposed on a lead body are found in, for example, U.S. Patent Application Publication Nos. 2012/0071949; 2012/0046710; 2012/0016378; 2011/0313500; 2011/0238129; 2011/0130818; 2011/0130817; 2011/0130816; 2011/0130803; 2011/0016378; 2011/0005069; and 2010/0268298, all of which are incorporated by reference.

It will be understood that the electrodes 434 may be formed in any suitable shape including, for example, round, oval, rectangular, pentagonal, cruciform, star-shaped, or the like. Any suitable number of electrodes 434 may be disposed along the distal end portion 404 of the lead body 406 including, for example, one, two, three, four, five, six, seven, eight, nine, ten, eleven, twelve, fourteen, sixteen, twenty, twenty-four, thirty, thirty-six, forty, forty-eight, fifty, or more electrodes 434.

In at least some embodiments, the electrodes 434 are configured and arranged for providing electrical stimulation to neural tissue. In which case, it may be advantageous to include electrodes 434 with shapes, sizes, and numbers that are suited for providing electrical stimulation to desired tissue, while also avoiding or reducing undesired stimulation of non-targeted tissue.

In at least some embodiments, the electrodes 434 are configured and arranged for facilitating placement of the lead 403 by sensing electrical activity in proximity to the current positioning of the electrodes 434. In which case, it may be advantageous to include electrodes 434 with shapes, sizes, and numbers that are suited for facilitating placement of the lead 403 in operational proximity to targeted neural tissue.

Figures 4D, 5A, 5B:
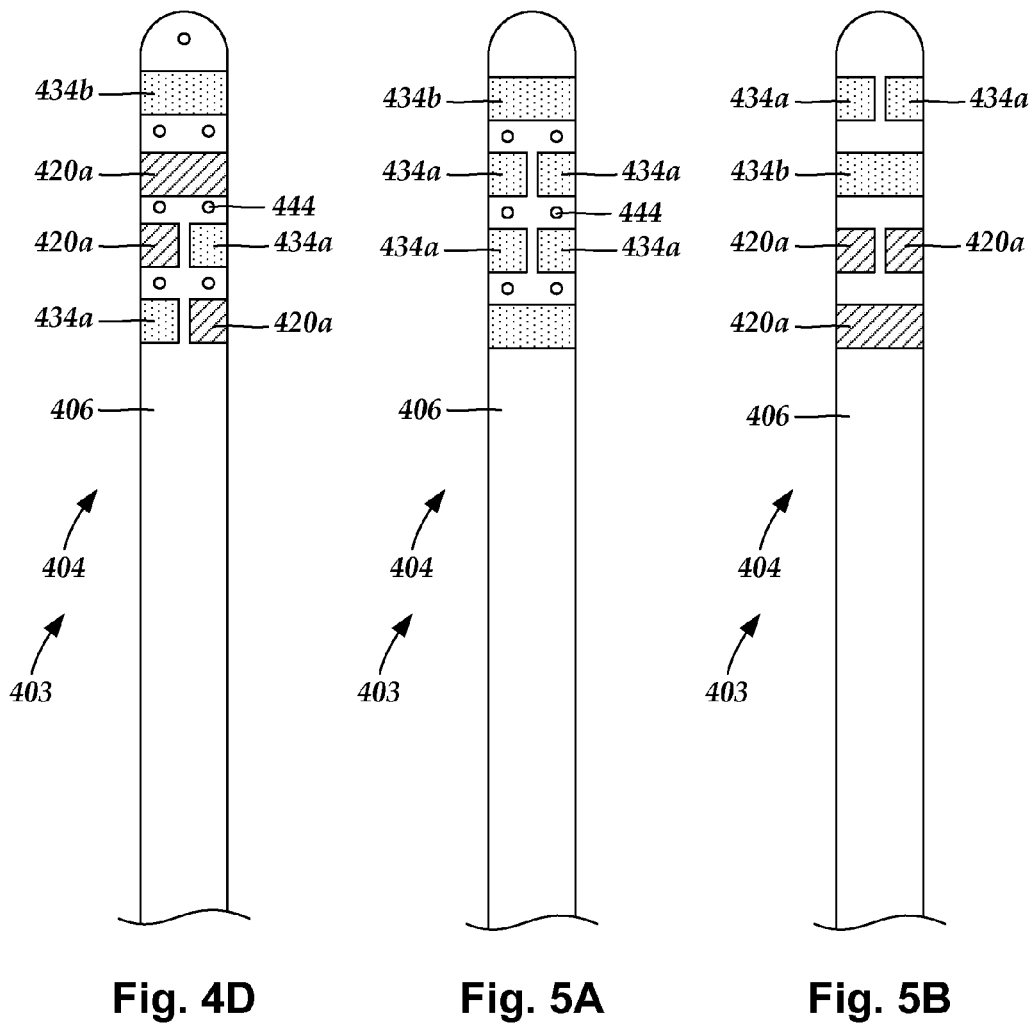
FIG. 4D is a schematic side view of a fourth embodiment of electrodes, light-emitters, and drug-dispensing ports disposed along a distal end portion of the lead body of FIG. 4A, according to the invention.
FIG. 5A is a schematic side view of one embodiment of electrodes and drug-dispensing ports disposed a distal end portion of the lead body of FIG. 4A, according to the invention.
FIG. 5B is a schematic side view of one embodiment of electrodes and light-emitters disposed along a distal end portion of the lead body of FIG. 4A, according to the invention.

In FIG. 4A, the electrodes 434 are shown disposed distally from the light-emitters 420 along the distal end portion 404 of the lead body 406. The light-emitters 420, electrodes 434, and drug-dispensing ports 444, however, can be disposed at the distal end portion 404 of the lead body 406 in any suitable arrangement relative to one another. FIGS. 4B-4D, provide several alternate arrangements of the light-emitters 420, electrodes 434, and drug-dispensing ports 444 from the embodiment shown in FIG. 4A.

FIG. 4B is a schematic side view of a second embodiment of the light-emitters 420, electrodes 434, and drug-dispensing ports 444 disposed along the distal end portion 404 of the lead body 406. FIG. 4C is a schematic side view of a third embodiment of the light-emitters 420, electrodes 434, and drug-dispensing ports 444 disposed along the distal end portion 404 of the lead body 406. FIG. 4D is a schematic side view of a fourth embodiment of the light-emitters 420, electrodes 434, and drug-dispensing ports 444 disposed along the distal end portion 404 of the lead body 406.

In FIG. 4B, the light-emitters 420 are shown disposed distally from the electrodes 434 along the distal end portion 404 of the lead body 406. Additionally, FIG. 4B shows the light-emitters 420 and the electrodes 434 each being exclusively segmented. In FIG. 4C, the light-emitters 420 and the electrodes 434 are disposed along the distal end portion 404 of the lead body 406 such that the light-emitters 420 and the electrodes 434 alternate along a longitudinal length of the lead body 406. Additionally, FIG. 4C shows the light-emitters 420 and the electrodes 434 each being exclusively ring-shaped. In FIG. 4D, the segmented light-emitters 420b and the segmented electrodes 434b are disposed along the distal end portion 404 of the lead body 406 such that at least some of the segmented light-emitters 420b and at least some of the segmented electrodes 434b alternate with one another around one or more particular circumferences of the lead body 406.

Turning to FIGS. 5A-5B, in at least some embodiments the lead 403 includes fewer elements from the embodiments of the lead body 406 shown in FIGS. 4A-4D. FIG. 5A illustrates a schematic side view of one embodiment of the distal end portion 404 of the lead body 406 without the light-emitters 420. In FIG. 5A, the electrodes 434 and the drug-dispensing ports 444 are disposed along the distal end portion 404 of the lead body 406. There are, however, no light-emitters 420 disposed on the lead body 406.

FIG. 5B illustrates a schematic side view of one embodiment of the distal end portion 404 of the lead body 406 without drug-dispensing ports 444. In FIG. 5B, the electrodes 434 and the light-emitters 420 are disposed along the distal end portion 404 of the lead body 406. There are, however, no drug-dispensing ports 444 disposed along the lead body 406.

Turning to FIGS. 6A-7E, in at least some embodiments the lead body 406 defines one or more lumens configured and arranged for facilitating operation of the one or more light-emitters 420, electrodes 434, and drug-dispensing ports 444. In at least some embodiments, one or more specific lumens are dedicated for one of the specific functions (e.g., providing light to the light-emitters, providing stimulation energy to the electrodes, or providing drugs to the drug-dispensing ports), while one or more other lumens are dedicated for providing another of the specific functions. In at least some embodiments, one or more lumens can be used for more than one specific function.

Figure 6A:
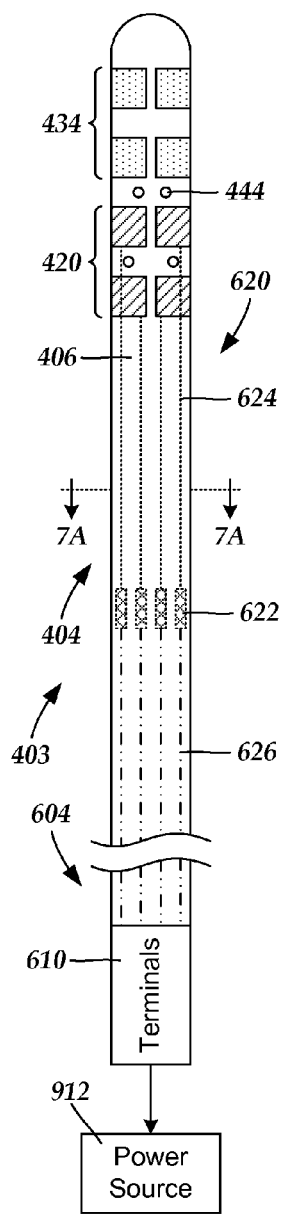
FIG. 6A is a schematic side view of one embodiment of the lead body of FIG. 4A and a power source, where a light-emitting assembly includes light-emitters disposed along a distal end portion of the lead body, light sources coupled to the light-emitters via optical transport media, and light source conductors coupled to the light sources and configured and arranged to couple to the power source via terminals disposed along a proximal end portion of the lead body, according to the invention.

In at least some embodiments, the light-emitters 420 are part of a light-emitting assembly. FIG. 6A illustrates a schematic side view of one embodiment of the lead 403 and a power source 912. The electrodes 434, the light-emitters 420, and the drug-dispensing ports 444 are disposed along the distal end portion 404 of the lead body. Terminals 610 are disposed along a proximal end portion 604 of the lead body 406.

A light-emitting assembly 620 is disposed, at least in part, along the lead 403. The light-emitting assembly 620 includes the light-emitters 420, as well as one or more light sources, such as light source 622, one or more optical transport media, such as optical transport medium 624, one or more light source conductors, such as light source conductor 626, and a power source, such as the power source 912 (which is discussed in more detail below, with reference to FIG. 9).

The light source 622 receives power from the power source 912 and converts the received power into light. In at least some embodiments, the light source 622 receives power via the light source conductors 626. In at least some embodiments, the light from the light source 622 is transported to the light-emitters 420 via optical transport media 624. In at least some embodiments, the power source is disposed in the control module (102 in FIG. 1). Alternately, the power source may be disposed on or in a stand-alone device that is external to the lead 403 and physically separated from the control module.

The light source 622 can be configured and arranged to convert the received power into light at any suitable wavelength to provide photonic stimulation. The light may include visible light, ultraviolet light, infrared light, or some combination thereof. In some embodiments, the light is produced at a single constant wavelength. In preferred embodiments, the light is produced at multiple wavelengths.

In at least some embodiments, the light-emitters 420 are any suitable device, or devices, suitable to emitting light received along the from the optical transport media 624 including, for example, distal ends of the optical transport media 624. Optionally, the light-emitting assembly 620 may include one or more light modulation devices including, for example, one or more lenses configured and arranged for focusing emitted light, one or more light directors configured and arranged for adjusting the direction of the emitted light, one or more filters to adjust one or more physical characteristics of emitted light, a polarizer for polarizing emitted light, or the like or combinations thereof. The light-emitting assembly 620 may also include other components that are disposed external to the lead body 406, such as an electronic subassembly for controlling one or more of the timing, duration, wavelengths, or amplitudes of the light emissions.

The optical transport media 624 can be any transport media suitable for providing a passage for transport of light including, for example, optical fibers, light pipes, light guides, light tubes, or the like or combinations thereof. Any suitable number of optical transport media 624 may be disposed along the lead body 406 including, for example, one, two, three, four, five, six, seven, eight, or more optical transport media 624. In at least some embodiments, each of the light-emitters 420 is coupled to a different optical transport medium 624.

The light source 622 can be any device suitable for converting power to light including, for example, light-emitting diodes. The light source 622 can be disposed anywhere along a longitudinal length of the lead body 406. In at least some embodiments, the light source 622 is disposed along the distal end portion 404 of the lead body 406. In at least some other embodiments, the light source 622 is disposed along a proximal end portion of the lead body 406. In at least some embodiments, the light source 622 is disposed along a portion of the lead body 406 that is proximal to a proximal-most electrode 402 and distal to a distal-most terminal 610. In at least some embodiments, the light source 622 is disposed in multiple locations along the longitudinal length of the lead body 406.

In yet other embodiments, the light source 622 is disposed external to the lead body 406. For example, in at least some embodiments the light source 622 is disposed on or in the control module (102 in FIG. 1). Alternately, the light source 622 may be external to the lead body 406 and physically separated from the control module. When the light source 622 is disposed external to the lead body, light generated from the light source 622 can, optionally, be input to the optical transport media 624 by directing the generated light into the optical transport media 624 via a proximal port 684 defined along the proximal end portion 604 of the lead body 406. Alternately, when the light source 622 is disposed external to the lead body, light generated from the light source 622 can be input to the optical transport media 624 by directing the generated light into an additional optical transport medium (e.g., one or more optical fibers, light pipes, light guides, light tubes, or the like or combinations thereof) that is disposed external to the lead body 406 and that couples the light source 622 to the proximal port 684.

Any suitable number of light sources 622 may be disposed along the lead body 406 including, for example, one, two, three, four, five, six, seven, eight, or more light sources 622. In at least some embodiments, each of the light-emitters 420 is coupled to a different light source 622. In at least some other embodiments, each of the light-emitters 420 may be coupled to the same light source 622. The one or more light sources 622 can be arranged into any suitable configuration. FIGS. 4B and 4C illustrate several different alternative light source 622 configurations.

Alternately, the light-emitters 420 can, themselves, be light sources 622. For example, the light-emitters 420 may be formed from light-emitting diodes disposed along the distal end portion 404 of the lead body 406. In which case, operational power can be provided to the light-emitters/light sources directly from the light source conductors 626.

Figure 6B:
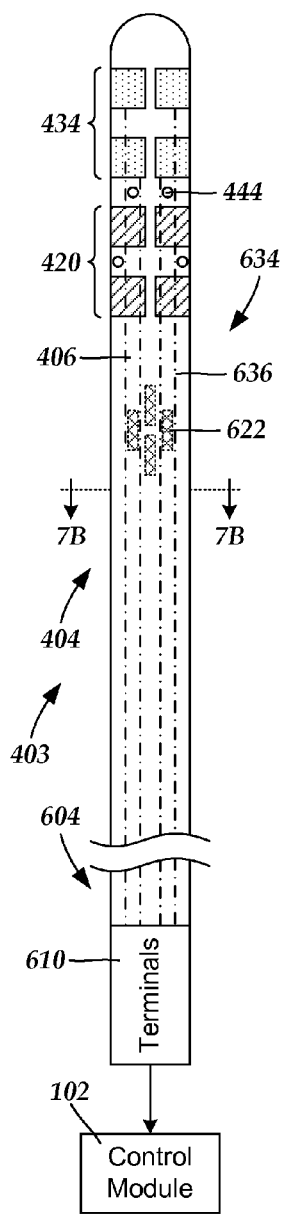
FIG. 6B is a schematic side view of one embodiment of the lead body of FIG. 4A and the control module of FIG. 1, where a stimulation assembly includes electrodes disposed along a distal end portion of the lead body, and electrical conductors coupling the electrodes to the control module via terminals disposed along a proximal end portion of the lead body, according to the invention.

In at least some embodiments, the electrodes 434 are part of a stimulation assembly. FIG. 6B illustrates a schematic side view of one embodiment of the lead 403 and the control module 102. The electrodes 434, the light-emitters 420, and the drug-dispensing ports 444 are disposed along the distal end portion 404 of the lead body. The terminals 610 are disposed along a proximal end portion 604 of the lead body 406.

A stimulation assembly 634 is disposed, at least in part, along the lead 403. The stimulation assembly 634 includes the electrodes 434, one or more stimulation assembly conductors, such as stimulation conductor 636, and the control module 102. The electrical connection between electrodes and the control module 102 are discussed above, with reference to FIGS. 1-3B. Additionally, components of the control module 102 are discussed in greater detail below, with respect to FIG. 9.

Figure 6C:
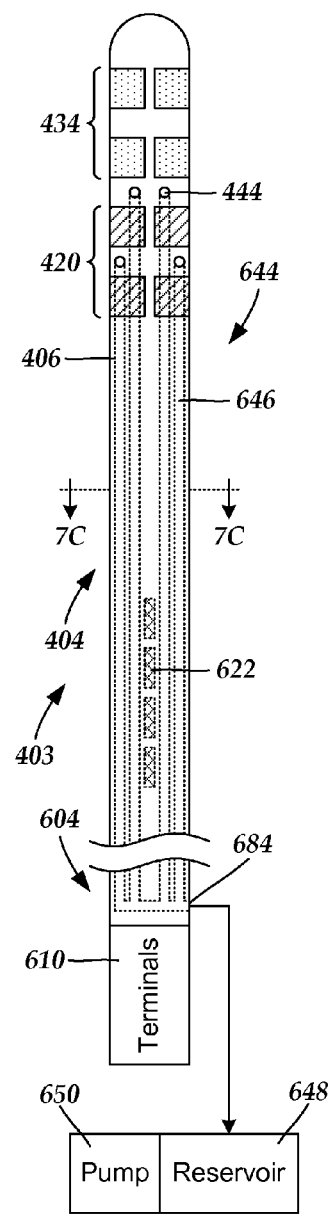
FIG. 6C is a schematic side view of one embodiment of the lead body of FIG. 4A and a drug reservoir, where a drug-dispensing assembly includes the drug reservoir, drug-dispensing ports disposed along a distal end portion of the lead body, and drug-delivery channels configured and arranged to couple the drug-dispensing ports to the drug reservoir, according to the invention.

In at least some embodiments, the drug-dispensing ports 444 are part of a drug-dispensing assembly. FIG. 6C illustrates a schematic side view of one embodiment of the lead 403 and a drug reservoir 648. The electrodes 434, the light-emitters 420, and the drug-dispensing ports 444 are disposed along the distal end portion 404 of the lead body. The terminals 610 are disposed along a proximal end portion 604 of the lead body 406.

A drug-dispensing assembly 644 is disposed, at least in part, along the lead 403. The drug-dispensing assembly 644 includes the drug-dispensing ports 444, one or more drug-delivery channels, such as drug-delivery channel 446, and the drug reservoir 648. The drug-dispensing ports 444, drug-delivery channels 646, and the drug reservoir 648 are all in fluid communication with one another such that drugs from the drug reservoir 648 are dispensable from the drug-dispensing ports 444 via the drug-delivery channels 446. The lead body 406 may define any suitable number of drug-delivery channels 646. In some embodiments, the lead body 406 defines a single drug-delivery channel 646.

In at least some embodiments, the drug reservoir 648 is disposed on or in the control module (102 in FIG. 1). Alternately, the drug reservoir 648 may be disposed on or in a stand-alone device that is external to the lead 403 and physically separated from the control module.

In at least some embodiments, the drug-dispensing assembly 644 is configured and arranged to function as a one-time assembly, where drugs within the drug reservoir 648 are dispensed only until the drug reservoir 648 is empty. In at least some other embodiments, the drug reservoir 648 is refillable. For example, in at least some embodiments the drug reservoir 648 includes a surface through which drugs may be input while the drug reservoir 648 is disposed in the patient (e.g., via a needle, a syringe, or the like) to refill the amount of drugs available for dispensing to the patient.

Optionally, the drug-dispensing assembly 644 further includes a pump 650 configured and arranged to facilitate movement of drugs from the drug reservoir 648 to the drug-dispensing ports 444. In at least some embodiments, the pump 650 is powered by the power source 912.

FIG. 7A is a schematic transverse cross-sectional view of one embodiment of the lead body 406, as shown in FIG. 6A. The lead body 406 shown in FIG. 7A defines a stylet lumen 702 and multiple optical lumens 704 each configured and arranged to receive the optical transport media 626.

FIG. 7B is a schematic transverse cross-sectional view of one embodiment of the lead body 406, as shown in FIG. 6B. The lead body 406 shown in FIG. 7B defines the stylet lumen 702 and multiple stimulation lumens 706 each configured and arranged to receive the stimulation conductors 636.

FIG. 7C is a schematic transverse cross-sectional view of one embodiment of the lead body 406, as shown in FIG. 6C. The lead body 406 shown in FIG. 7C defines the stylet lumen 702 and multiple drug-delivery channels 646 each configured and arranged to receive drugs for dispensing from the drug-dispensing ports 444.

FIG. 7D is a schematic transverse cross-sectional view of one embodiment of the lead body 406, where the lead body defines a stylet lumen 702, optical lumens 704, stimulation lumens 706, and drug-delivery channels 646. In FIG. 7D, a single optical transport medium 624 is shown disposed in each of the optical lumens 704 and a single stimulation conductor 636 is shown disposed in each of the stimulation lumens 706.

In FIGS. 7A-7D, four optical lumens 704, four stimulation lumens 706, and four drug-delivery channels 646 are shown corresponding with four optical transport media 624, four stimulation conductors 636, and four drug-dispensing ports 444, respectively, respectively. It will be understood that, in at least some embodiments, the lead 403 includes additional (or fewer) light-emitters, or electrodes, or drug-dispensing ports from the embodiments of the lead 403 shown in FIGS. 7A-7D. In which case, the lead body 406 defines additional (or fewer) lumens/channels 704, 706, and 646 to accommodate the additional (or fewer) light-emitters, electrodes, or drug-dispensing ports.

In FIGS. 7A-7D, a single optical transport medium 624 is shown disposed in each of the optical lumens 704, and a single stimulation conductor 636 is shown disposed in each of the stimulation lumens 706. It will be understood that, in at least some embodiments, multiple optical transport media 624 can be disposed in one or more of the optical lumens 704, multiple stimulation conductors 636 can be disposed in one or more of the stimulation lumens 706, or both.

In FIGS. 7A-7D, separate lumens are used to house each of the optical transport media, the stimulation conductors, and the drugs. It will be understood that, in at least some embodiments, combination lumens may be used to house combinations of one or more optical transport media, one or more stimulation conductors, or one or more drug-delivery channels.

FIG. 7E is a schematic transverse cross-sectional view of another embodiment of the lead body 406. The lead body 406 shown in FIG. 7E defines the stylet lumen 702, the multiple drug-delivery channels 646, and multiple combination lumens 712. As shown in FIG. 7E the combination lumens 712 are configured and arranged to receive optical transport media 624 and stimulation conductors 636. In alternate embodiments, the combination lumens 712 are configured and arranged to house one or more of the drug-delivery channels in addition to optical transport media 624 and stimulation conductors 636, or in lieu of either the optical transport media 624 or the stimulation conductors 636.

In FIGS. 4A-7E, the light-emitting assembly 620, the stimulation assembly 634, and the drug-delivery assembly 644 are each shown disposed along an isodiametric (e.g., percutaneous) lead. It will be understood that the light-emitting assembly 620, the stimulation assembly 634, and the drug-delivery assembly 644 may be disposed on any suitable type of lead. In at least some embodiments, the light-emitting assembly 620, the stimulation assembly 634, and the drug-delivery assembly 644 are disposed on a paddle lead.

Figure 8A:
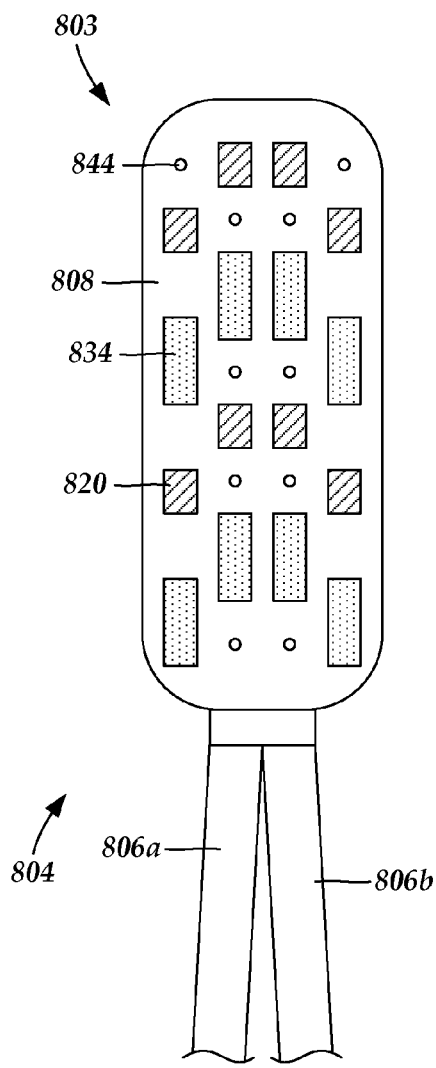
FIG. 8A is a schematic side view of one embodiment of a paddle body disposed along a distal end portion of two lead bodies, where electrodes, light-emitters, and drug-dispensing ports are disposed along the paddle body, according to the invention.
Figure 8B:
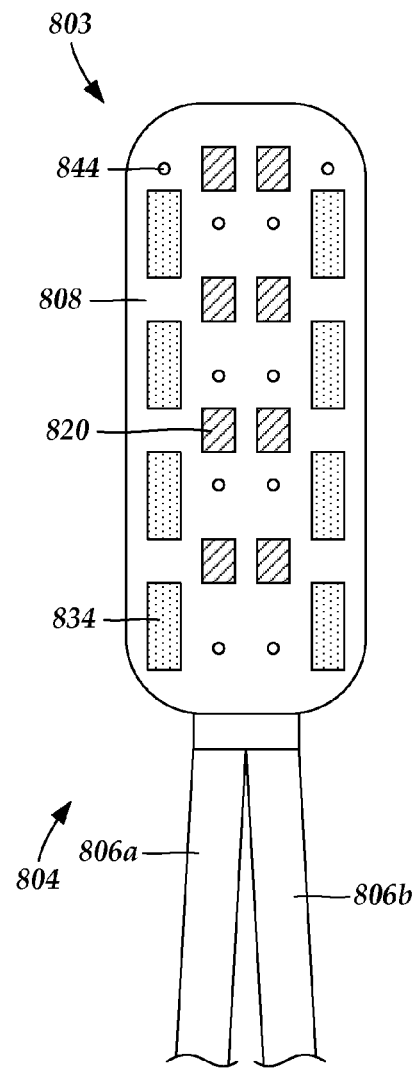
FIG. 8B is a schematic side view of another embodiment of the paddle body of FIG. 8A disposed along a distal end portion of the lead bodies of FIG. 8A, where electrodes, light-emitters, and drug-dispensing ports are disposed along the paddle body, according to the invention.

FIGS. 8A-8B illustrate embodiments of light-emitters, electrodes, and drug-dispensing ports disposed on paddle leads. FIG. 8A is a schematic side view of one embodiment of a paddle lead 803. The paddle lead 803 includes a paddle body 804 disposed along distal end portions 804 of two lead bodies 806a and 806b. Light-emitters 820, electrodes 834, and drug-dispensing ports 844 are disposed along the paddle body 804. FIG. 8B is a schematic side view of another embodiment of the paddle body 804 disposed along a distal end portions 804 of the lead bodies 806a and 806b. FIG. 8B also includes light-emitters 820, electrodes 834, and drug-dispensing ports 844 disposed along the paddle body 804.

Figure 9:
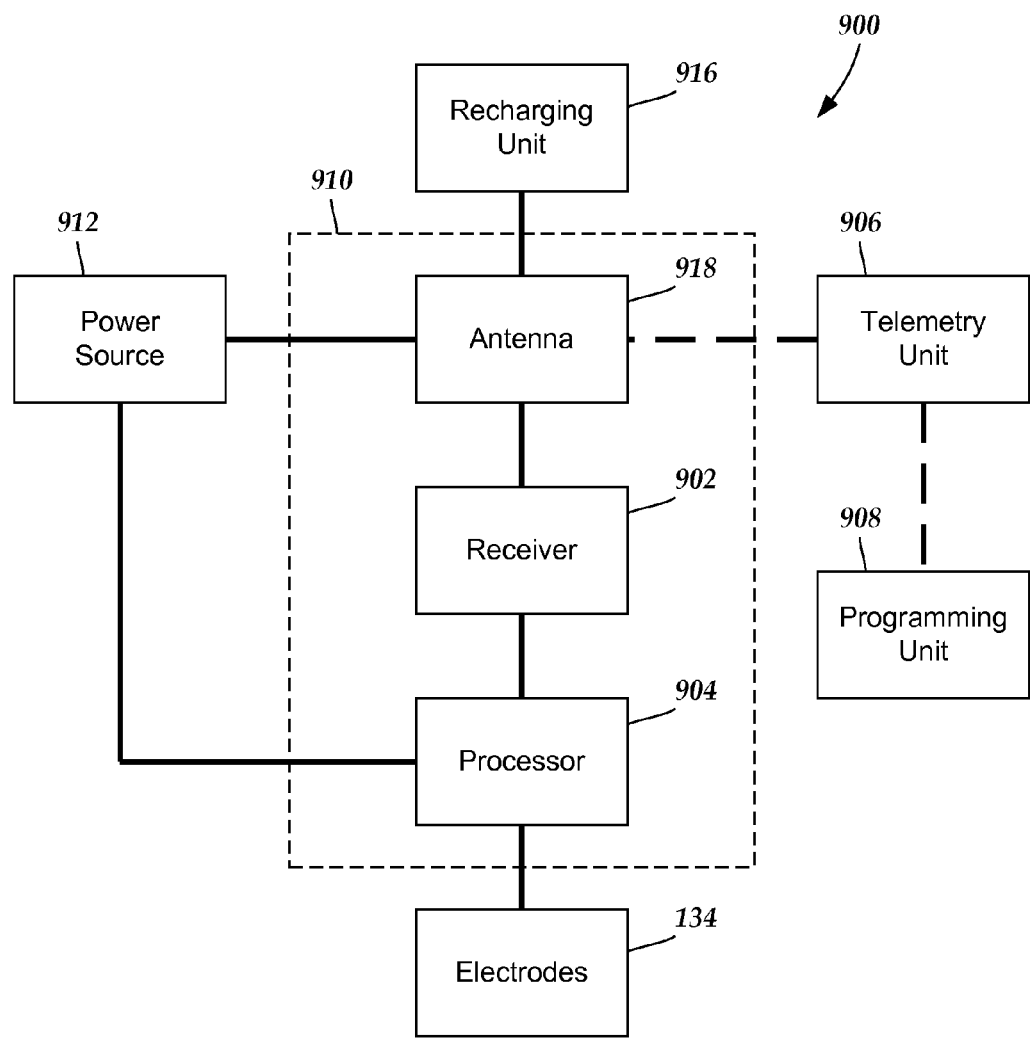
FIG. 9 is a schematic overview of one embodiment of components of a stimulation system, including an electronic subassembly disposed within a control module, according to the invention.

FIG. 9 is a schematic overview of one embodiment of components of an electrical stimulation system 900 including an electronic subassembly 910 disposed within a control module. It will be understood that the electrical stimulation system can include more, fewer, or different components and can have a variety of different configurations including those configurations disclosed in the stimulator references cited herein.

Some of the components (for example, a power source 912, an antenna 918, a receiver 902, and a processor 904) of the electrical stimulation system can be positioned on one or more circuit boards or similar carriers within a sealed housing of an implantable pulse generator, if desired. Any power source 912 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 918 or a secondary antenna. The external power source can be in a device that is mounted on the skin of the user or in a unit that is provided near the user on a permanent or periodic basis.

If the power source 912 is a rechargeable battery, the battery may be recharged using the optional antenna 918, if desired. Power can be provided to the battery for recharging by inductively coupling the battery through the antenna to a recharging unit 916 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. The processor 904 is generally included to control the timing and electrical characteristics of the electrical stimulation system. For example, the processor 904 can, if desired, control one or more of the timing, frequency, strength, duration, and waveform of the pulses. In addition, the processor 904 can select which electrodes can be used to provide stimulation, if desired. In some embodiments, the processor 904 selects which electrode(s) are cathodes and which electrode(s) are anodes. In some embodiments, the processor 904 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 908 that, for example, allows modification of pulse characteristics. In the illustrated embodiment, the processor 904 is coupled to a receiver 902 which, in turn, is coupled to the optional antenna 918. This allows the processor 904 to receive instructions from an external source to, for example, direct the pulse characteristics and the selection of electrodes, if desired.

In one embodiment, the antenna 918 is capable of receiving signals (e.g., RF signals) from an external telemetry unit 906 which is programmed by the programming unit 908. The programming unit 908 can be external to, or part of, the telemetry unit 906. The telemetry unit 906 can be a device that is worn on the skin of the user or can be carried by the user and can have a form similar to a pager, cellular phone, or remote control, if desired. As another alternative, the telemetry unit 906 may not be worn or carried by the user but may only be available at a home station or at a clinician's office. The programming unit 908 can be any unit that can provide information to the telemetry unit 906 for transmission to the electrical stimulation system 900. The programming unit 908 can be part of the telemetry unit 906 or can provide signals or information to the telemetry unit 906 via a wireless or wired connection. One example of a suitable programming unit is a computer operated by the user or clinician to send signals to the telemetry unit 906.

The signals sent to the processor 904 via the antenna 918 and the receiver 902 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 900 to cease operation, to start operation, to start charging the battery, or to stop charging the battery. In other embodiments, the stimulation system does not include the antenna 918 or receiver 902 and the processor 904 operates as programmed.

Optionally, the electrical stimulation system 900 may include a transmitter (not shown) coupled to the processor 904 and the antenna 918 for transmitting signals back to the telemetry unit 906 or another unit capable of receiving the signals. For example, the electrical stimulation system 900 may transmit signals indicating whether the electrical stimulation system 900 is operating properly or not or indicating when the battery needs to be charged or the level of charge remaining in the battery. The processor 904 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An electrical stimulation lead, comprising:
   at least one lead body having a distal end portion, a proximal end portion, an outer surface, and a longitudinal length;
   a plurality of electrodes disposed along the distal end portion of the at least one lead body;
   a plurality of terminals disposed along the proximal end portion of the at least one lead body;
   a plurality of stimulation conductors, each stimulation conductor of the plurality of stimulation conductors electrically coupling each of the plurality of terminals to at least one of the plurality of electrodes;
   at least one light-emitter disposed along the distal end portion of the at least one lead body, the at least one light-emitter configured and arranged for emitting received light outward from the outer surface of the at least one lead body;
   at least one light source disposed along the at least one lead body, the at least one light source configured and arranged for converting received electrical power into light;
   at least one optical transport medium disposed along the at least one lead body, the at least one optical transport medium having a proximal end coupled to the at least one light source and a distal end coupled to the at least one light-emitter, wherein the at least one optical transport medium is configured and arranged to transport light from the at least one light source to the at least one light-emitter; and
   at least one light source conductor electrically coupled to the at least one light source and extending to the plurality of terminals.

2. The electrical stimulation lead of claim 1, wherein the at least one light source is disposed along the proximal end portion of the at least one lead body.

3. The electrical stimulation lead of claim 1, wherein the at least one light source is disposed in the at least one lead body at a location that is proximal to a proximal-most electrode of the plurality of electrodes and distal to a distal-most terminal of the plurality of terminals.

4. The electrical stimulation lead of claim 1, wherein the at least one light source is a light-emitting diode.

5. The electrical stimulation lead of claim 1, further comprising a paddle body disposed along the distal end portion of the at least one lead body.

6. The electrical stimulation lead of claim 5, wherein the plurality of electrodes are disposed along the paddle body.

7. The electrical stimulation lead of claim 5, further comprising at least one drug-dispensing port defined along the paddle body; and at least one drug-delivery channel in fluid communication with the at least one drug-dispensing port, the at least one drug-delivery channel extending along the longitudinal length of the at least one lead body to the paddle body.

8. The electrical stimulation lead of claim 5, wherein the at least one light-emitter is disposed along the paddle body.

9. The electrical stimulation lead of claim 1, further comprising:
at least one drug-dispensing port defined along the distal end portion of the at least one lead body; and
at least one drug-delivery channel in fluid communication with the at least one drug-dispensing port, the at least one drug-delivery channel extending along the longitudinal length of the at least one lead body to the proximal end portion of the at least one lead body.

10. An electrical stimulating system comprising:
the electrical stimulation lead of claim 9,
a control module coupleable to the electrical stimulation lead, the control module comprising
a housing, and
an electronic subassembly disposed in the housing;
a power source configured and arranged for providing power to the at least one light source via the at least one light source conductor;
a drug reservoir configured and arranged for providing drugs to the at least one drug-dispensing port via the at least one drug-delivery channel; and
a connector for receiving the electrical stimulation lead, the connector having a proximal end, a distal end, and a longitudinal length, the connector comprising
a connector housing defining a port at the distal end of the connector, the port configured and arranged for receiving the proximal end portion of the at least one lead body of the electrical stimulation lead, and
a plurality of connector contacts disposed in the connector housing, the plurality of connector contacts configured and arranged to couple to at least one of the plurality of terminals disposed on the proximal end of the at least one lead body of the electrical stimulation lead.

11. The electrical stimulation system of claim 10, wherein the power source is disposed on or in the control module.

12. The electrical stimulation system of claim 10, wherein the drug reservoir is disposed on or in the control module.

13. The electrical stimulation system of claim 10, wherein at least one of the power source or the drug reservoir is a stand-alone device that is external to the at least one lead body and physically separated from the control module.

14. The electrical stimulation system of claim 10, further comprising a pump configured and arranged to facilitate providing drugs from the drug reservoir to the at least one drug-dispensing port via the at least one drug-delivery channel.

15. A method for providing gene therapy to a patient using an electrical stimulation system, the method comprising:
advancing the electrical stimulation lead of claim 9 into the patient with the distal end portion of the at least one lead body of the electrical stimulation lead disposed in operational proximity to a target therapy location within the patient;
dispensing at least one drug from the at least one drug-dispensing port; and
emitting light from the at least one light-emitter of the electrical stimulation lead to photonically stimulate patient tissue at the target stimulation location.

16. The method of claim 15, further comprising emitting stimulation energy from the plurality of electrodes of the electrical stimulation lead to electrically stimulate patient tissue at the target stimulation location.

17. The method of claim 15, wherein advancing the electrical stimulation lead of claim 1 into the patient comprises using the plurality of electrodes of the electrical stimulation lead to facilitate advancement of the electrical stimulation lead.

18. An electrical stimulation lead, comprising:
at least one lead body having a distal end portion, a proximal end portion, an outer surface, and a longitudinal length;
a plurality of electrodes disposed along the distal end portion of the at least one lead body;
a plurality of terminals disposed along the proximal end portion of the at least one lead body;
a plurality of stimulation conductors, each stimulation conductor of the plurality of stimulation conductors electrically coupling each of the plurality of terminals to at least one of the plurality of electrodes;
at least one light-emitter disposed along the distal end portion of the at least one lead body, the at least one light-emitter configured and arranged for receiving power, converting the received power to light, and emitting the converted light outward from the outer surface of the at least one lead body;
at least one light source conductor coupled to the at least one light-emitter and extending to the plurality of terminals;
at least one drug-dispensing port defined along the distal end portion of the at least one lead body; and
at least one drug-delivery channel in fluid communication with the at least one drug-dispensing port, the at least one drug-delivery channel extending along the longitudinal length of the at least one lead body to the proximal end portion of the at least one lead body.

19. The electrical stimulation lead of claim 18 wherein the at least one light emitter is a light-emitting diode.

20. An electrical stimulation lead assembly, comprising:
an electrical stimulation lead comprising
at least one lead body having a distal end portion, a proximal end portion, an outer surface, and a longitudinal length,
a paddle body disposed along the distal end portion of the at least one lead body;
a plurality of electrodes disposed on a surface of the paddle body,
a plurality of terminals disposed along the proximal end portion of the at least one lead body,
a plurality of stimulation conductors, each stimulation conductor of the plurality of stimulation conductors electrically coupling each of the plurality of terminals to at least one of the plurality of electrodes,
at least one light-emitter disposed along the paddle body, the at least one light-emitter configured and arranged for emitting received light outward from the surface of the paddle body,
at least one optical transport medium disposed along the at least one lead body, the at least one optical transport medium having a distal end coupled to the at least one light-emitter and a proximal end extending to the proximal end portion of the at least one lead body, wherein the at least one optical transport medium is configured and arranged to transport light,
at least one drug-dispensing port defined along the surface of the paddle body, and
at least one drug-delivery channel in fluid communication with the at least one drug-dispensing port, the at least one drug-delivery channel extending along the longitudinal length of the at least one lead body to the proximal end portion of the at least one lead body; and at least one light source disposed external to the at least one lead body and in communication with the at least one optical transport medium, the at least one light source configured and arranged for generating light, the at least one light source coupled to the at least one light-emitter via the at least one optical transport medium.

* * * * *